United States Patent [19]
Heaven et al.

[11] Patent Number: 5,957,939
[45] Date of Patent: Sep. 28, 1999

[54] MEDICAL DEVICE FOR DEPLOYING SURGICAL FABRICS

[75] Inventors: Malcolm D. Heaven, Laguna Hills, Calif.; Pamela Shellhammer, Somerset, N.J.

[73] Assignee: Imagyn Medical Technologies, Inc., Newport Beach, Calif.

[21] Appl. No.: 08/904,354

[22] Filed: Jul. 31, 1997

[51] Int. Cl.[6] .................................................. A61B 17/00
[52] U.S. Cl. ............................................................. 606/151
[58] Field of Search ................................. 606/151, 190, 606/191, 192; 604/13, 15, 11, 286, 264

[56] References Cited

U.S. PATENT DOCUMENTS

| | | | |
|---|---|---|---|
| 5,304,187 | 4/1994 | Green et al. | 606/151 |
| 5,503,623 | 4/1996 | Tilton, Jr. | 604/13 |

*Primary Examiner*—Michael Buiz
*Assistant Examiner*—Vikki Trinh
*Attorney, Agent, or Firm*—Burns, Doane, Swecker & Mathis, L.L.P.

[57] ABSTRACT

A medical device for deploying surgical fabric at an operative site within a body cavity of a patient. The device includes a deploying member in the form of an elongated inserter shaft with a supporting member in the form of a sheet of plastic attached to a distal end of the shaft. A sheet of surgical fabric is placed on the supporting member and rolled around the inserter shaft. An introducer tube surrounds the rolled-up fabric and supporting member to prevent them from unrolling. The introducer tube may then be inserted into the body cavity and retracted to allow the supporting member to self-unwind the fabric sheet within the body cavity. The device may also provide for irrigation of the surgical site.

20 Claims, 6 Drawing Sheets

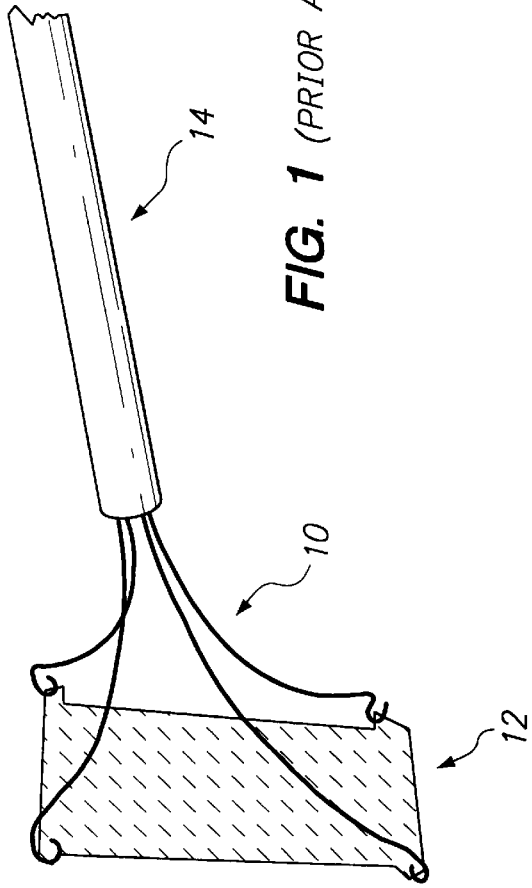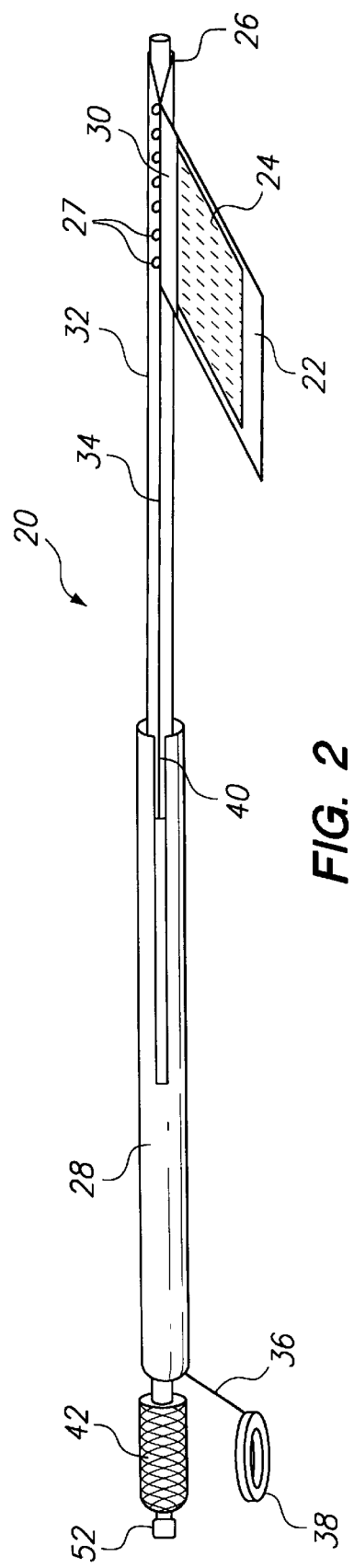

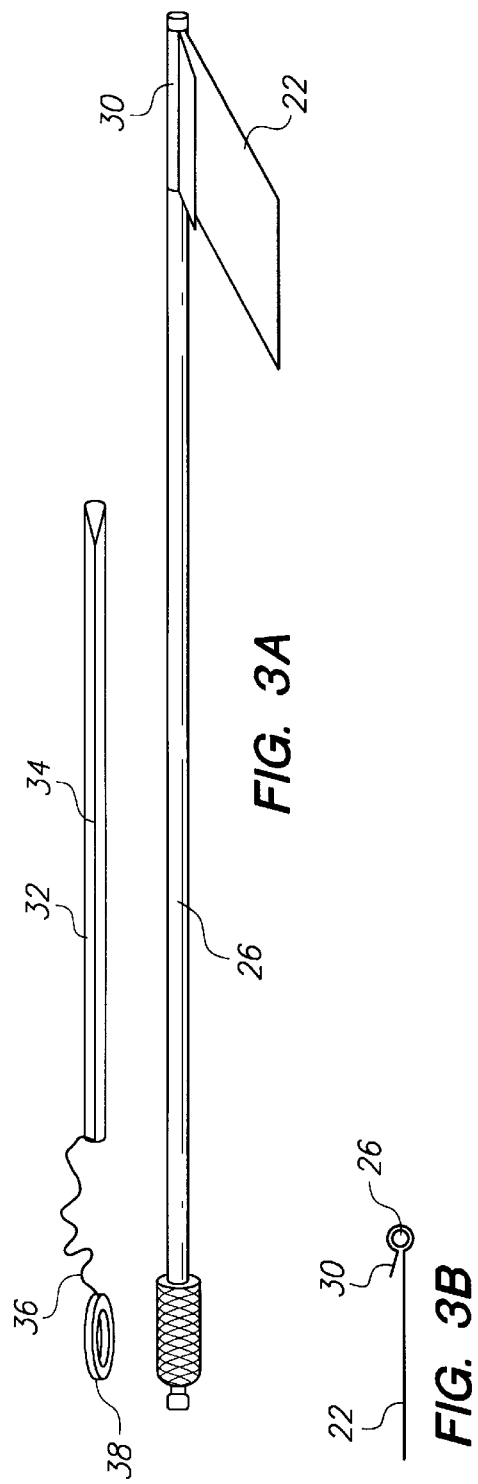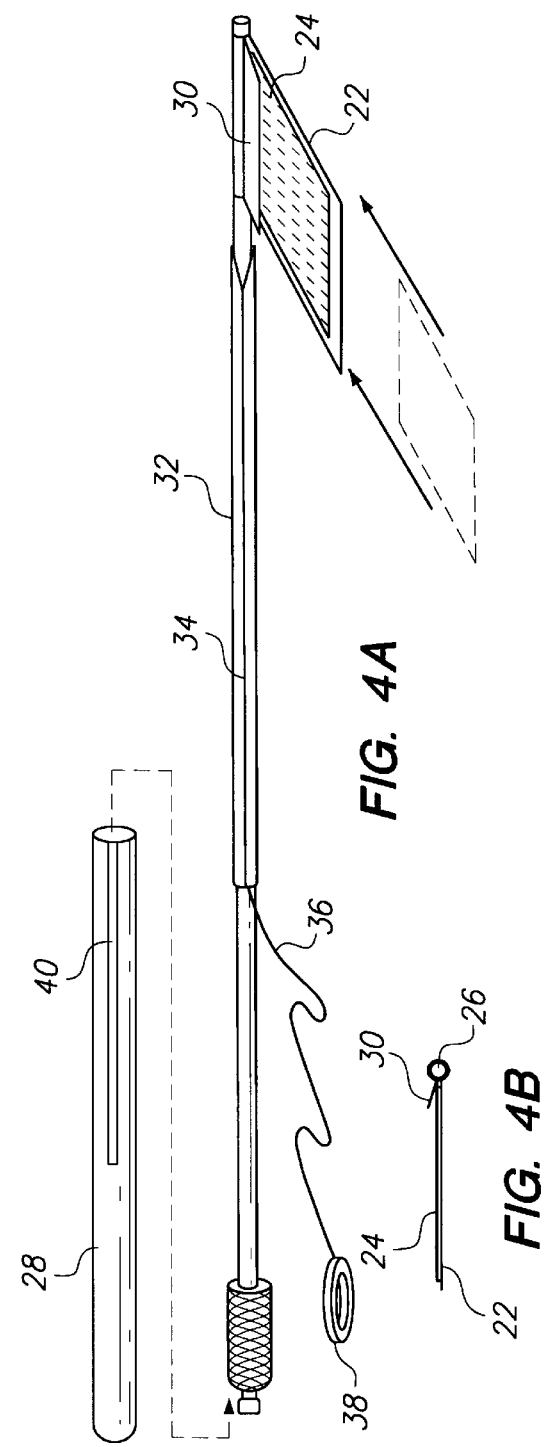

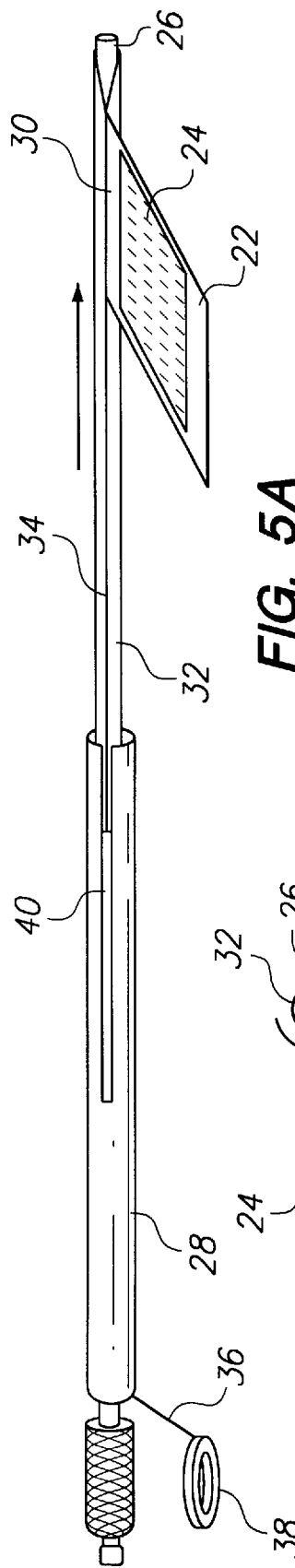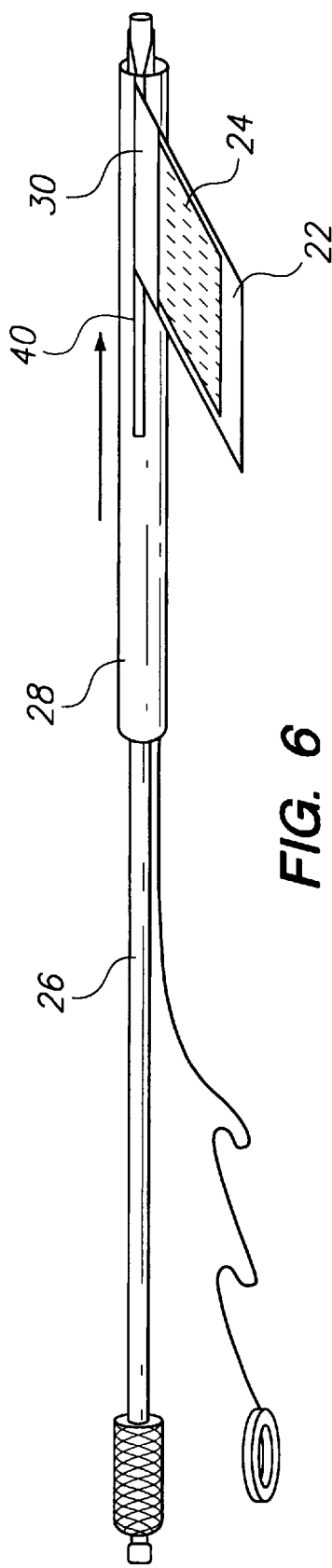

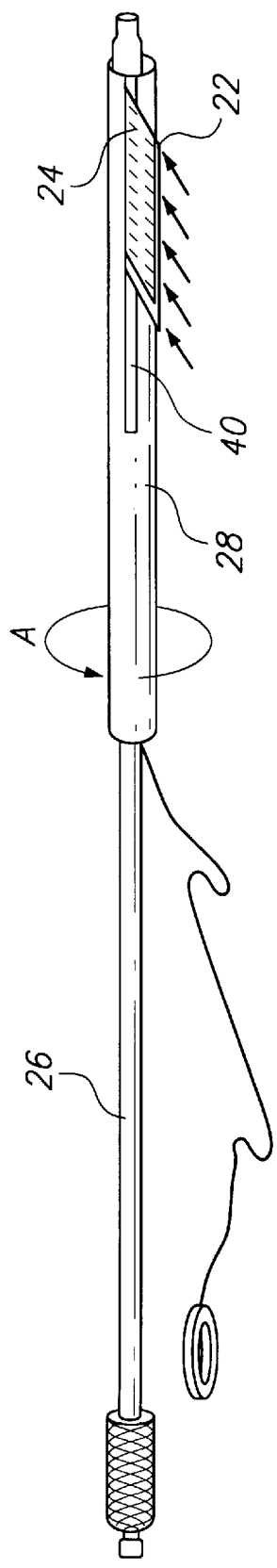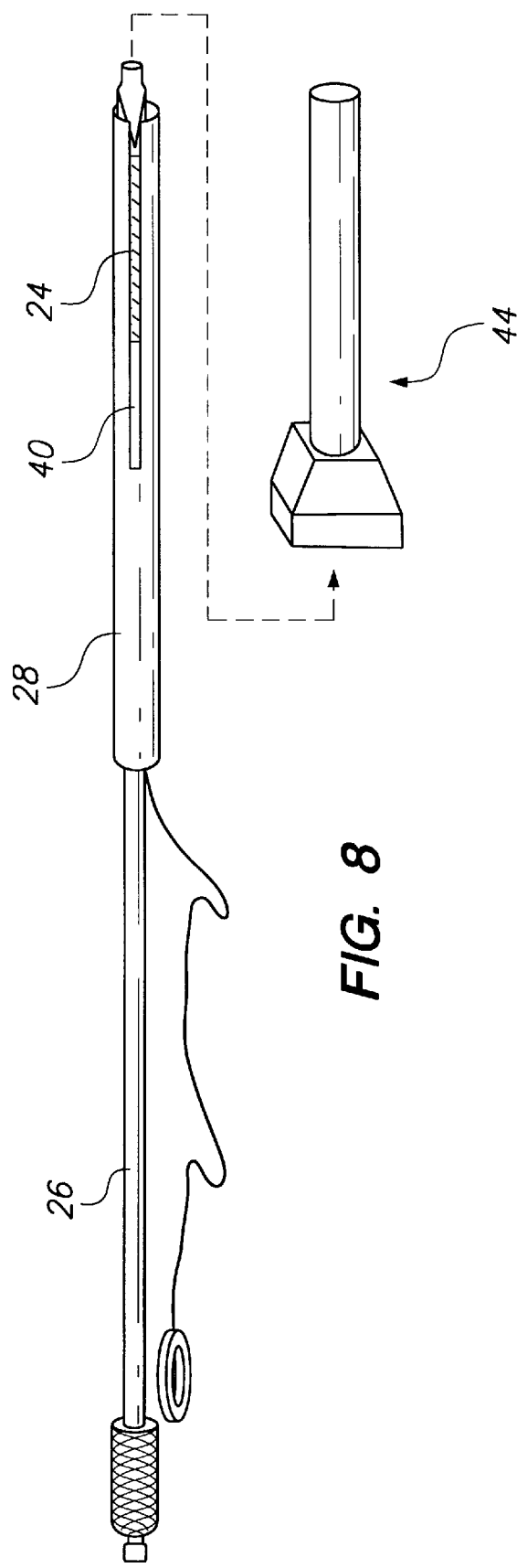
FIG. 7
FIG. 8

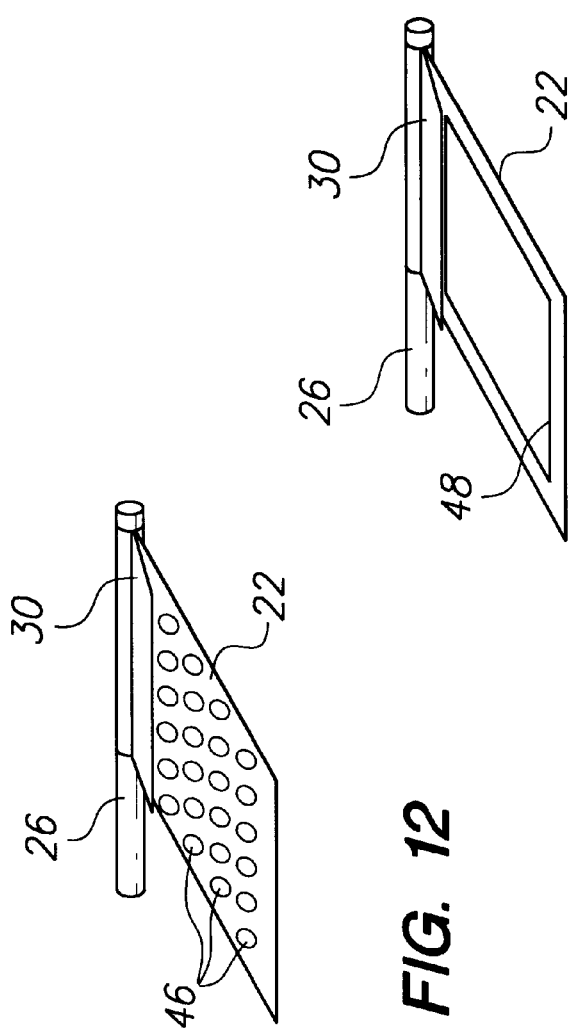
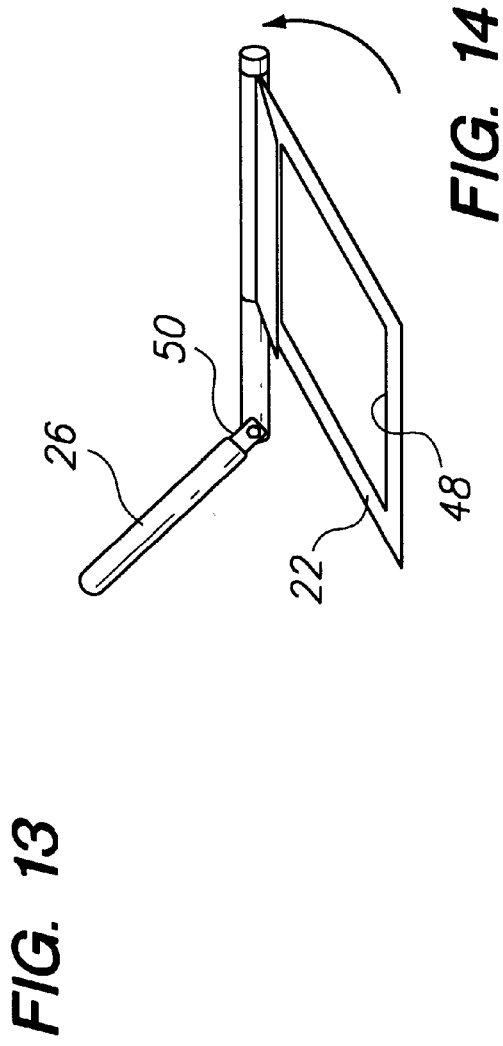

MEDICAL DEVICE FOR DEPLOYING SURGICAL FABRICS

BACKGROUND OF THE INVENTION

The invention relates to a medical device, and more particularly to a medical device useful during minimally invasive procedures, such as laparoscopic procedures, for conveniently deploying a sheet of fabric within the abdominal cavity.

During minimally invasive types of surgery such as laparoscopic procedures it is sometimes necessary to spread out a sheet of fabric within a body cavity and adhere the fabric to a tissue mass. An example of such a procedure is hernia repair wherein sheets of fabric such as woven polyolefin fabrics are used. In addition, woven fabrics manufactured from oxidized cellulose are used in gynecologic pelvic surgery and in other procedures to reduce the tendency for the formation of adhesions. For instance, see U.S. Pat. Nos. 5,279,539, 5,134,229, 5,002,551 and 4,840,626.

Deployment of sheets of fabric in a controlled manner within a body cavity is difficult, particularly in the case of bioabsorbable fabrics made from oxidized cellulose, which once wet become tacky and have a tendency to bond to themselves and to adjacent surfaces. A prior art device for deploying fabric sheets is shown in FIG. 1. This device includes spring elements 10 which hook into the corners of the fabric 12 to be deployed. The spring elements and fabric are compressed and loaded in a delivery tube 14. Upon exiting the delivery tube 14 the spring elements 10 spread apart, deploying the fabric 12. However, in practice these devices are difficult to use because it is difficult to attach and release the fabric 12 from the spring elements 10, and loading the bunched up fabric and spring elements in the delivery tube 14 is also difficult. Such a device is manufactured by Cabot Medical.

U.S. Pat. No. 5,258,000 discloses a device for deploying fabrics wherein a thin superelastic Nitinol wire, or similar springy material, is threaded through the material to be deployed. The material is then folded or rolled around an introducer and contained in a delivery tube. On exiting the delivery tube the wire springs out to its preferred, unconstrained state, deploying the fabric. The disadvantage of this approach is that generally, once the fabric has been tacked or bonded in place, the wire must be left in or withdrawn carefully from the periphery of the material without dislodging it. It is also somewhat laborious to place the wire around the edges of the fabric in the first place.

SUMMARY OF THE INVENTION

The invention provides a medical device for deploying surgical fabric within a body cavity of a patient. The device includes a deploying member having a proximal end and a distal end. The device further includes a clamping member supported at the distal end of the deploying member for holding the fabric in rolled and unrolled configurations. The clamping member is engageable with a portion of a piece of surgical fabric and rotatable with respect to the deploying member so that the fabric in the unrolled configuration can be wrapped around the clamping member to the rolled configuration. The device further includes a self-unwinding member at the distal end of the deploying member, the self-unwinding member being effective in automatically unwinding the fabric from the rolled configuration to the unrolled configuration.

According to a preferred embodiment of the invention, the self-unwinding member includes a support member attached to the distal end of the deploying member and an introducer tube surrounding the deploying member. The support member includes a support surface for receiving the fabric and is rollable along with the fabric from an unrolled to a rolled condition. The introducer tube is movable from a first position at which the support member is in the unrolled condition to a second position at which the introducer tube surrounds the support member and holds the support member in the rolled condition. The support member can be a resilient thin sheet of relatively stiff plastic which returns to a substantially flat shape when the introducer tube is moved to the first position. The introducer tube can include a slot engageable with the support member for guiding the support member into the introducer tube when the support member is rolled to the rolled condition.

The device can include a capturing tube slidable over the clamping member when the fabric is rolled around the clamping member. The clamping member can comprise a moveable flap which moves towards and away from the support member to engage only an edge of the fabric. The capturing tube is movable to a position at which it surrounds the deploying member and presses the flap against the support member. The device can include a drawstring attached to the capturing tube and extending through the introducer tube to allow the capturing tube to be retracted by pulling on the drawstring. The deploying member can be articulated and can include at least one fluid passage for irrigation or suction of fluids at an operative site within a patient.

The invention also provides a method for deploying a sheet of surgical fabric within a body cavity. The method includes steps of inserting a deploying member attached to a rolled-up sheet of fabric within an introducer tube into a body cavity, retracting the introducer tube along the deploying member so as to expose the rolled-up sheet of fabric and deploy the fabric by self-unwinding the fabric, and moving the deploying member and placing the unrolled sheet of fabric at a desired site within the body cavity.

According to a preferred embodiment, the deploying member includes a resilient deploying sheet and the sheet of fabric is located in overlying relationship on the deploying sheet, the deploying sheet being self-unwound during the step of retracting the introducer tube. The placing step can include pressing on a side of the deploying sheet opposite to a side on which the sheet of fabric is located whereby the fabric can be pressed against tissue at the operative site. The sheet of fabric can be released from the deploying member by releasing a clamping member. For instance, the sheet of fabric can be released by retracting a capturing tube which holds a flap of the clamping member against an edge of the fabric. The method can further include a step of irrigating an operative site within the body cavity by passing fluid through the deploying member.

BRIEF DESCRIPTION OF THE DRAWING FIGURES

The invention will be described in greater detail with reference to the accompanying drawings in which like elements bear like reference numerals.

FIG. 1 is a perspective view of a prior art device for deploying fabric;

FIG. 2 is a perspective view of a device according to the present invention;

FIG. 3a is a perspective view of the device of FIG. 2 prior to assembly;

FIG. 3b is an end view of the device shown in FIG. 3a;

FIG. 4a is a perspective view of the device of FIG. 2 with a sheet of fabric inserted under the flap;

FIG. 4b is an end view of the device of FIG. 4a;

FIG. 5a is a perspective view of the device of FIG. 2 with the capture tube slid forward to trap the sheet of fabric;

FIG. 5b is an end view of the device of FIG. 5a;

FIG. 6 is a perspective view of the device of FIG. 2 with the delivery tube slid forward;

FIG. 7 is a perspective view of the device of FIG. 2 showing the delivery tube being rotated;

FIG. 8 is a perspective view of the device of FIG. 2 ready for insertion into a trocar cannula;

FIG. 12 is a perspective view of the support film according to a second embodiment of the invention;

FIG. 13 is a perspective view of the support film according to a third embodiment of the invention; and FIG. 14 is a perspective view of a fourth embodiment of the invention having an articulated end.

DETAILED DESCRIPTION OF THE PREFERRED EMBODIMENTS

Figure 9:
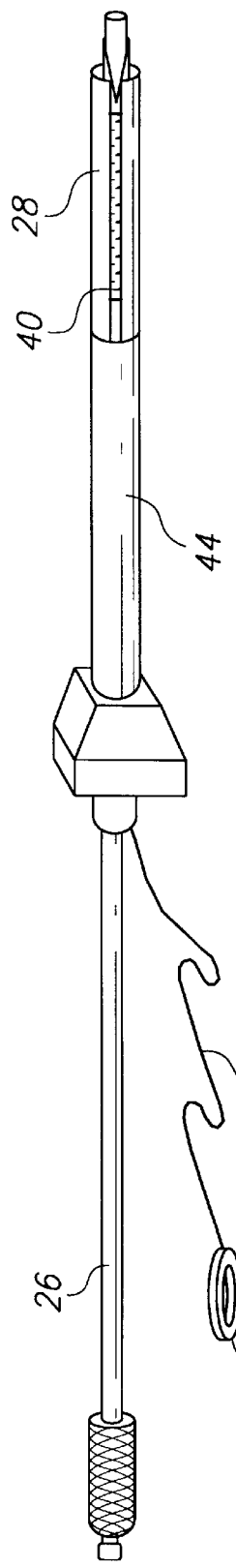
FIG. 9 is a perspective view of the device of FIG. 2 positioned in a trocar cannula.

The device of the invention overcomes deficiencies of the prior art, and offers substantially more control and versatility. The device according to the invention also offers a unique delivery system for surgical fabric which incorporates a self-actuating system which fully deploys the fabric as a flat sheet and allows the sheet to be pressed against a tissue mass.

A preferred embodiment of the medical device for deploying fabrics according to the invention includes an insertion member having a proximal end and a distal end and a fabric supporting member attached to the distal end of the insertion member. The fabric supporting member is adapted to be rolled around the insertion member and can be held in place with an introducer tube. The introducer tube is adapted to be positioned around at least a portion of the rolled fabric supporting member to prevent the fabric supporting member from unrolling.

The invention also relates to a method for deploying a sheet of surgical fabric within a body cavity including the steps of providing an insertion member and an introducer tube, rolling a sheet of surgical fabric around the insertion member and inserting the insertion member with the rolled sheet of fabric therearound into the introducer tube. The distal end of the introducer tube is then inserted into a body cavity and the sheet of fabric is released from the introducer tube so as to be in an unrolled condition within the body cavity.

The invention relates to a new and improved medical device 20 for delivering various surgical fabric materials to a site of a surgical operation within the body of a patient. The device will be useful in the field of laparoscopic procedures involving the placement of sheet-like surgical fabric, e.g., polypropylene mesh for hernia repair, or oxidized cellulose mesh for the prevention of adhesions.

The device 20 includes a relatively flat (in the unrolled condition) but rollable support member 22 which acts as a support layer for a fabric sheet 24. The support member 22 comprises a sheet of non-adherent material such as plastic which is bonded or otherwise mounted on a central support shaft 26 which is used for inserting the fabric 24 into a body cavity. In use, the support member 22 and the overlying fabric sheet 24 are rolled up together around the support shaft 26 and then prevented from unrolling, or unfurling, by an axially slidable introducer tube 28 advanced over the rolled layers. Upon retraction of the introducer tube 28, the inherent resilience of the plastic sheet of support member 22 causes the plastic sheet to self-unwind, and as a consequence the fabric 24 is also unrolled, and presented in a highly desirable, spread out and flat, manner.

The plastic sheet of support member 22 serves an additional purpose once the assembly has been unrolled within the bodily cavity, in that the surgeon can press the fabric sheet 24 into contact with the desired site by pushing with a tool on an exposed surface of the plastic sheet rather than on the fabric. This provides a particular advantage with oxidized cellulose fabric in that the plastic sheet prevents a wet instrument such as a grasper from sticking to the cloth and causing handling and placement problems.

The plastic sheet of support member 22 can be rectangular or any desirable shape. For instance, the plastic sheet may be configured to match any shape of a fabric sheet to be deployed. Thus, the plastic sheet of support member 22 may or may not be the same size as the fabric sheet. Further, the plastic sheet of support member 22 may be reusable or detachable so that it may be replaced. Alternatively, the entire device may be disposable.

According to a preferred embodiment of the invention the support member 22 comprises a resilient plastic sheet of rectangular shape which is bonded or otherwise mounted on the central support shaft 26. Any suitable plastic material may be used, so long as it is biocompatible, and has sufficient resilience, or elastic modulus, to ensure that it will self-unwind to an unrolled configuration from a rolled configuration once the introducer tube is removed. It is also feasible to use non-plastic materials such as thin metal sheets or strips, or other materials that will be apparent to those skilled in the art.

The plastic sheet is preferably attached to the support shaft 26 in a manner which provides a short overlying flap 30 for clamping the fabric sheet 24 against the plastic sheet of support member 22, as shown in FIGS. 3a and 3b. In use, the fabric sheet 24 to be delivered to a body cavity is placed on the upper surface of the support member 22 with an edge of the fabric sheet positioned under the flap 30, as shown in FIGS. 4a and 4b.

The device includes a resilient capturing tube 32 having a longitudinal slit 34. The capturing tube 32 is configured to fit snugly over the central support shaft 26 and secure the fabric sheet in place by pressing the flap 30 against the support member 22. The longitudinal slit 34 is preferably provided with a V-shaped opening at a free end thereof for ease in guiding the flap 30 and support member 22 into the slit 34. The other end of the capturing tube 32 is attached in a suitable manner to a string 36 which is provided with a pull ring 38. The string 36 is of sufficient length to extend through the introducer tube 28 to a position externally of the patient when the device is in use in a body cavity of the patient. The capturing tube 32 may be made from any suitable bio-compatible material which has sufficient strength to press the support member 22 against the flap 30 and thus maintain the fabric material in the rolled-up state. The tube 32 can be made from polyolefin or semi-rigid PVC or other materials apparent to those skilled in the art.

The introducer tube 28 is of a sufficient diameter to allow the introducer tube 28 to slide over the support member 22 and the fabric sheet 24 when they are rolled up around the support shaft 26. The introducer tube 28 is provided with a slot 40 which may be used to guide support member 22 into the introducer tube as the support member 22 is rolled around the shaft 26 either by rotating the introducer tube 28 relative to the shaft 26 or vice versa. This rolling operation may be performed either inside or outside of a body cavity.

It is also possible to incorporate a series of ports 27 along the length of shaft 26, in which case the shaft 26 is hollow and sealed at its distal end. The ports 27 can be used for irrigation or aspiration of a surgical site. For instance, a source of fluid or suction may be attached to a fluid port 52 (e.g., standard luer connection) provided at the end of handle 42. The ports 27 can be used to inject fluids, for example, sterile saline solution may be injected to wet the fabric if required, and to promote adhesion. The incorporation of this feature relieves the surgeon of the need to insert a separate device in order to achieve irrigation or aspiration.

The operation of the device 20 according to a preferred embodiment of the invention is shown in FIGS. 3–11. FIG. 3a shows a perspective view of the support member 22 and the capturing tube 32 prior to assembly. As shown in FIG. 3b, the flap 30 is in an open position for receiving a sheet of fabric.

As shown in FIGS. 4a and 4b, the capturing tube 32 is positioned on the support shaft and a fabric sheet 24 is placed on the support member 22 with an edge of the fabric sheet placed under the flap 30. As shown in FIGS. 5a and 5b, the fabric sheet 24 is clamped in position by sliding the close fitting capturing tube 32 forward so that the slit of the capturing tube engages the flap 30 on one side and the support member 22 on the opposite side and presses them together.

As shown in FIGS. 6 and 7, the introducer tube 28 is then advanced so that the slot 40 in the introducer tube receives the support member 22 and flap 30. The fabric sheet 24 and the support member 22 are then simultaneously rolled or furled around the support shaft 26 by rotating the introducer tube 28 with respect to the support shaft 26 as indicated by the arrow A in FIG. 7 and thus drawing the support member and fabric in through the slot 40 and simultaneously furling and capturing the two layers. Alternatively, the introducer tube 28 may be held stationary and the support shaft 26 may be rotated by the handle 42. The introducer tube 28 holds the rolled material in place, ready for delivery to the surgical site, as shown in FIG. 8.

Figure 10:
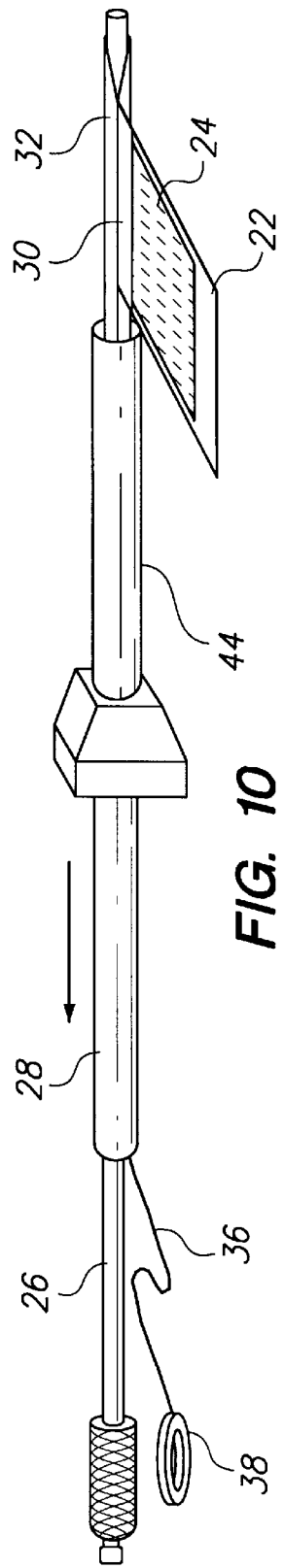
FIG. 10 is a perspective view of the device of FIG. 2 with the delivery tube withdrawn and the fabric unfurled.

The device 20 can be inserted through a trocar cannula 44 as shown in FIG. 9. Once the device is positioned within a body cavity the introducer tube 28 is retracted axially along the support shaft 26, thus exposing the rolled up fabric and support member 22 as shown in FIG. 10. Upon retraction of the introducer tube 28, the plastic sheet of support member 22 self-unwinds to its preferred substantially flat unfurled configuration thereby unrolling the fabric sheet 24. The unrolled fabric sheet 24 may now be directed to the desired site with the device and pressed into place by applying modest pressure on the back of the plastic sheet of support member 22. To facilitate bonding of the fabric, if required, water or saline solution may be directed to the fabric 24 via the ports 27 in support shaft 26.

Figure 11:
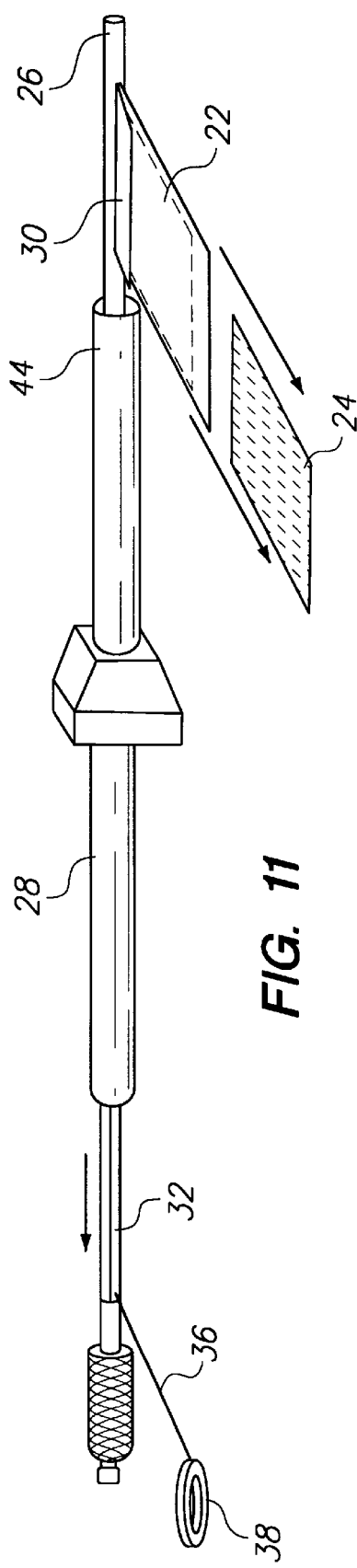
FIG. 11 is a perspective view of the device of FIG. 2 with the capture tube withdrawn and the fabric sheet released from the flap.

Once the fabric 24 is in place, the capturing tube 32 is retracted along the support shaft 26 by pulling on the pull ring 38, as shown in FIG. 11, thus raising the flap 30 and releasing the fabric 24 from the support member 22. The support member 22 can then be withdrawn into the trocar cannula 44 using a combination of shaft rotation and pulling or, in the case of a slotted introducer tube 28, refurling support member 22 as previously described and shown in FIG. 7. The device can then be reused for another piece of fabric, if required. Alternatively, the body of the device can be reusable and the support member 22 can be replaced. However, the entire device can be disposable, if desired.

An alternative embodiment of the support member 22, shown in FIG. 12, has perforations 46. These perforations 46 do not materially detract from the support member's overall resilience while allowing water or saline to be selectively directed at the fabric through the support member using a suction/irrigation device or similar instrument.

Another alternative embodiment of the support member 22 is shown in FIG. 13. This embodiment includes a large access window 48 which exposes a large area of the fabric 24 without impairing the ability of the support member 22 to unfurl the fabric. This embodiment is useful in draping the fabric sheet 24 over irregular surfaces.

Other means for fixing the fabric sheet 24 to the support member 22, such as a water soluble adhesive, could be used instead of the combination of the flap 30 and the capturing tube 32. For instance, the water soluble adhesive could be dissolved when a saline solution or water spray is used to tack the fabric to the surgical site. It is also feasible that a fabric/support member assembly could be pre-packaged and supplied in a sterilized condition for use with the aforementioned reusable embodiment.

Another embodiment shown in FIG. 14, is provided with a hinge 50 in the support shaft 26 which allows the end of a support shaft having the support member thereon to pivot. For instance, one or more pull wires (not shown) could be incorporated in the shaft 26 for controlling the degree of bending of the support shaft. The articulation of the tip of the support shaft allows for an extra degree of freedom and may assist with ease of placing the fabric.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A medical device for deploying surgical fabric within a body cavity of a patient comprising:
   a deploying member having a proximal end and a distal end;
   a clamping member supported at the distal end of the deploying member for holding the fabric in rolled and unrolled configurations, the clamping member being engageable with a portion of a piece of said surgical fabric and rotatable with respect to the deploying member so that the fabric in the unrolled configuration can be wrapped around the clamping member to the rolled configuration; and
   means for automatically unwinding the fabric from the rolled configuration to the unrolled configuration.

2. The medical device of claim 1, wherein the means includes a support member and an introducer tube, the support member being attached to the distal end of the deploying member, the support member including a support surface for receiving the fabric and being rollable along with the fabric from an unrolled to a rolled condition, the introducer tube surrounding the deploying member, the introducer tube being movable from a first position at which the support member is in the unrolled condition to a second position at which the introducer tube surrounds the support member and holds the support member in the rolled condition.

3. The medical device of claim 2, further comprising a sheet of surgical fabric attached to the clamping member, the fabric overlying a surface of the support member.

4. The medical device of claim 2, wherein the clamping member comprises a flap movable towards and away from the support member and a capturing tube which surrounds the deploying member and presses the flap against the support member.

5. The medical device of claim 4, further comprising a drawstring attached to the capturing tube, the drawstring extending through the introducer tube and allowing the capturing tube to be retracted along the deploying member by pulling on the drawstring.

6. The medical device of claim 1, further comprising a capturing tube slidable over the clamping member when the fabric is in the rolled configuration.

7. The medical device of claim 1, wherein the clamping member engages only an edge of the fabric.

8. The medical device of claim 1, wherein the means comprises a thin sheet of stiff plastic.

9. The medical device of claim 2, wherein the support member comprises a sheet of plastic.

10. The medical device of claim 1, wherein the deploying member is articulated so that a distal end of the deploying member is bendable.

11. The medical device of claim 1, wherein the deploying member includes at least one fluid passage for irrigation or suction of fluids at an operative site within a patient.

12. The medical device of claim 1, further comprising a sheet of surgical fabric attached to the clamping member.

13. A medical device for deploying surgical fabric within a body cavity of a patient comprising:
    a deploying member having a proximal end and a distal end;
    a clamping member supported at the distal end of the deploying member for holding the fabric in rolled and unrolled configurations, the clamping member being engageable with a portion of a piece of said surgical fabric and rotatable with respect to the deploying member so that the fabric in the unrolled configuration can be wrapped around the clamping member to the rolled configuration; and
    a self-unwinding member at the distal end of the deploying member, the self-unwinding member being effective in automatically unwinding the fabric from the rolled configuration to the unrolled configuration;
    the self-unwinding member including a support member and an introducer tube, the support member being attached to the distal end of the deploying member, the support member including a support surface for receiving the fabric and being rollable along with the fabric from an unrolled to a rolled condition, the introducer tube surrounding the deploying member, the introducer tube being movable from a first position at which the support member is in the unrolled condition to a second position at which the introducer tube surrounds the support member and holds the support member in the rolled condition, the support member comprising a resilient sheet which returns to a substantially flat shape when the introducer tube is moved to the first position.

14. The medical device of claim 13, wherein the introducer tube includes a slot engageable with the support member for guiding the support member into the introducer tube when the support member is rolled to the rolled condition.

15. A method for deploying a sheet of surgical fabric within a body cavity comprising steps of:
    inserting a deploying member attached to a rolled-up sheet of fabric within an introducer tube into a body cavity;
    retracting the introducer tube along the deploying member so as to expose the rolled-up sheet of fabric and deploy the fabric by means for self-unwinding the fabric; and
    moving the deploying member and placing the unrolled sheet of fabric at a desired site within the body cavity.

16. A method for deploying a sheet of surgical fabric within a body cavity comprising steps of:
    inserting a deploying member attached to a rolled-up sheet of fabric within an introducer tube into a body cavity;
    retracting the introducer tube along the deploying member so as to expose the rolled-up sheet of fabric and deploy the fabric by self-unwinding the fabric; and
    moving the deploying member and placing the unrolled sheet of fabric at a desired site within the body cavity, the deploying member including a resilient deploying sheet and the sheet of fabric being located in overlying relationship on the deploying sheet, the deploying sheet being self-unwound during the step of retracting the introducer tube.

17. The method for deploying a sheet of fabric as claimed in claim 16, wherein the placing step includes pressing on a side of the deploying sheet opposite to a side on which the sheet of fabric is located so as to press the fabric against tissue at the operative site.

18. The method for deploying a sheet of fabric as claimed in claim 15, further comprising releasing the sheet of fabric from the deploying member by releasing a clamping member.

19. The method for deploying a sheet of fabric as claimed in claim 18, wherein the sheet of fabric is released by retracting a capturing tube which holds a flap of the clamping member against an edge of the fabric.

20. The method of deploying a sheet of fabric as claimed in claim 15, further comprising a step of irrigating an operative site within the body cavity by passing fluid through the deploying member.

* * * * *